United States Patent [19]
Stevenson et al.

[11] Patent Number: 6,066,619
[45] Date of Patent: May 23, 2000

[54] NON-AQUEOUS PROTIC PEPTIDE FORMULATIONS

[75] Inventors: Cynthia L. Stevenson, Mountain View; Sally A. Tao, San Jose; Steven J. Prestrelski, Mountain View; James B. Eckenhoff, Los Altos; Jeremy C. Wright, Los Altos; John J. Leonard, Jr., Cupertino, all of Calif.

[73] Assignee: Alza Corporation, Mt. View, Calif.

[21] Appl. No.: 09/293,172

[22] Filed: Apr. 16, 1999

Related U.S. Application Data

[63] Continuation of application No. 08/874,680, Jun. 13, 1997
[60] Provisional application No. 60/022,129, Jul. 18, 1996.

[51] Int. Cl.$^7$ ............... A61K 38/00; C07K 5/00; C07K 7/00
[52] U.S. Cl. ............... 514/12; 514/15; 530/313; 530/328
[58] Field of Search ........... 514/12, 15; 530/313, 530/328; 424/600, 40

[56] References Cited

U.S. PATENT DOCUMENTS

| | | | |
|---|---|---|---|
| 3,914,412 | 10/1975 | Gendrich et al. | 424/177 |
| 4,547,370 | 10/1985 | Roeske | 514/15 |
| 4,661,472 | 4/1987 | Rivier et al. | 514/15 |
| 4,689,396 | 8/1987 | Roeske et al. | 530/313 |
| 4,851,385 | 7/1989 | Roeske | 514/15 |
| 5,034,229 | 7/1991 | Magruder et al. | 424/422 |
| 5,057,318 | 10/1991 | Magruder et al. | 424/438 |
| 5,110,596 | 5/1992 | Magruder et al. | 424/438 |
| 5,198,533 | 3/1993 | Schally et al. | 530/313 |
| 5,480,868 | 1/1996 | Kamei et al. | 514/15 |

FOREIGN PATENT DOCUMENTS

| | | |
|---|---|---|
| 0 312 052 | 4/1989 | European Pat. Off. . |
| 0 432 479 | 6/1991 | European Pat. Off. . |
| 0432479 | 6/1991 | European Pat. Off. ......... A61K 9/48 |
| 0 510 731 | 10/1992 | European Pat. Off. . |
| WO92/20711 | 11/1992 | WIPO . |
| 9406452 | 3/1994 | WIPO ............... A61K 37/02 |
| WO94/06452 | 3/1994 | WIPO . |
| WO94/19020 | 9/1994 | WIPO . |
| WO95/00168 | 1/1995 | WIPO . |
| WO95/04540 | 2/1995 | WIPO . |
| WO97/27840 | 8/1997 | WIPO . |

OTHER PUBLICATIONS

Factrel (gonadorelin HCI for subcutaneous or IV injection), *Physician's Desk Ref.*, 50th Ed., pp. 2877–2878 (1996).
Fu Lu, et al., "Percutaneous Absorption Enhancement of Leuprolide", *Pharm. Res.*, 9/12, pp. 1575–1576 (1992).
Helm, et al., "Stability of Gonadorelin and Triptorelin in Aqueous Solution", *Pharm. Res.*, 7/12, pp. 1253–1256 (1990).
Johnson, et al., "Degradation of the LH–RH Analog Nafarelin Acetate in Aqueous Solution", *Intl. J. Pharm.*, 31, pp. 125–129 (1986).
Lupron (leuprolide acetate for subcutaneous injection), *Physician's Desk Ref.*, 50th Ed., pp. 2555–2556 (1996).
Lupron Depot (leuprolide acetate for depot suspension), *Physician's Desk Ref.*, 50th Ed., pp. 2556–2562 (1996).
Lutrepulse (gonadorelin acetate for IV injection), *Physician's Desk Ref.*, 50th Ed., pp. 980–982 (1996).
Okada, et al., "New Degradation Product of Des–Gly$^{10}$–NH$_2$–LH–RH–Ethylamide (Fertirelin) in Aqueous Solution", *J. Pharm. Sci.*, 80/2, pp. 167–170 (1991).
Okada, et al., "Preparation of Three–Month Depot Injectable Microspheres of Leuprorelin Acetate Using Biodegradable Polymers", *Pharm. Res.*, 11/8, pp. 1143–1147 (1994).
Oyler, et al., "Characterization of the Solution Degradation Products of Histrelin, a Gonadotropin Releasing Hormone (LH/RH) Agonist", *J. Pharm. Sci.*, 80/3, pp. 271–275 (1991).
Powell, et al., "Parenteral Peptide Formulations: Chemical and Physical Properties of Native Luteinizing Hormone–Releasing Hormone (LHRH) and Hydrophobic Analogues in Aqueous Solution", *Pharm. Res.*, 8/10, pp. 1258–1263 (1991).
Powell, et al., "Peptide Liquid Crystals: Inverse Correlation of Kinetic Formation and Thermodynamic Stability in Aqueous Solution", *Pharm. Res.*, 11/9, pp. 1352–1354 (1994).
Powers, et al., "Solution Behavior of Leuprolide Acetate, an LHRH Agonist, as Determined by Circular Dichroism Spectroscopy", *Int. J. Pharm.*, 108, pp. 49–55 (1994).
Shi, et al., "Long–Term Stability of Aqueous Solutions of Luteinizing Hormone–Releasing Hormone Assessed by an In–Vitro Bioassay and Liquid Chromatography", *J. Pharm. Sci.*, 73/6, pp. 819–821 (1984).
Toguchi, "Pharmaceutical Manipulation of Leoprorelin Acetate to Improve Clinical Performance", *J. Int. Med. Res.*, 18, pp. 35–41 (1990).
Zoladex (goserelin acetate implant), *Physician's Desk Ref.*, 50th Ed., pp. 2858–2861 (1996).

*Primary Examiner*—Avis M. Davenport
*Attorney, Agent, or Firm*—Mary Ann Dillahunty; Steven F. Stone; Pauline A. Clarke

[57] ABSTRACT

This invention relates to stable non-aqueous protic formulations of peptide compounds. These stable formulations comprise peptide in non-aqueous protic solvent. They may be stored at elevated temperatures for long periods of time and are especially useful in implantable delivery devices for long term delivery of drug.

13 Claims, 11 Drawing Sheets

NON-AQUEOUS PROTIC PEPTIDE FORMULATIONS

This application is a continuation of application Ser. No. 08/874,680, filed Jun. 13, 1997.

This application claims priority under 35 U.S.C. 119(e) to U.S. application Ser. No. 60/022,129 filed Jul. 3, 1996, the disclosure of which is incorporated herein by reference.

FIELD OF THE INVENTION

This invention relates to stable non-aqueous protic formulations of peptide compounds. In particular, formulations with high concentrations of peptide compounds are provided.

BACKGROUND OF THE INVENTION

References

The following references are referred to by numbers in brackets ([]) at the relevant portion of the specification.
1. Zoladex (goserelin acetate implant), Physician's Desk Reference, 50th Edition, pages 2858–2861 (1996).
2. U.S. Pat. No. 3,914,412, issued Oct. 21, 1975.
3. U.S. Pat. No. 4,547,370, issued Oct. 15, 1985.
4. U.S. Pat. No. 4,661,472, issued Apr. 28, 1987.
5 U.S. Pat. No. 4,689,396, issued Aug. 25, 1987.
6 U.S. Pat. No. 4,851,385, issued Jul. 25, 1989.
7. U.S. Pat. No. 5,198,533, issued Mar. 30, 1993.
8. U.S. Pat. No. 5,480,868, issued Jan. 2, 1996.
9. WO92/20711, published Nov. 26, 1992.
10. WO95/00168, published Jan. 5, 1995.
11. WO95/04540, published Feb. 16, 1995.
12. "Stability of Gonadorelin and Triptorelin in Aqueous Solution", V. J. Helm, B. W. Muller, *Pharmaceutical Research*, 7/12, pages 1253–1256 (1990).
13. "New Degradation Product of Des-Gly$^{10}$—NH$_2$—LHRH-Ethylamide (Fertirelin) in Aqueous Solution", J. Okada, T. Seo, F. Kasahara, K. Takeda, S. Kondo, *J. of Pharmaceutical Sciences*, 80/2, pages 167–170 (1991).
14. "Characterization of the Solution Degradation Product of Histrelin, a Gonadotropin Releasing Hormone (LHRH) Agonist", A. R. Oyler, R. E. Naldi, J. R. Lloyd, D. A. Graden, C. J. Shaw, M. L. Cotter, *J. of Pharmaceutical Sciences*, 80/3, pages 271–275 (1991).
15. "Parenteral Peptide Formulations: Chemical and Physical Properties of Native Luteinizing Hormone-Releasing Hormone (LHRH) and Hydrophobic Analogues in Aqueous Solution", M. F. Powell, L. M. Sanders, A. Rogerson, V. Si, *Pharmaceutical Research*, 8/10, pages 1258–1263 (1991).
16. "Degradation of the LHRH Analog Nafarelin Acetate in Aqueous Solution", D. M. Johnson, R. A. Pritchard, W. F. Taylor, D. Conley, G. Zuniga, K. G. McGreevy, *Intl. J. of Pharmaceutics*, 31, pages 125–129 (1986).
17. "Percutaneous Absorption Enhancement of Leuprolide", M. Y. Fu Lu, D. Lee, G. S. Rao, Pharmaceutical Research, 9/12, pages 1575–1576 (1992).
18. Lutrepulse (gonadorelin acetate for IV injection), Physician's Desk Reference, 50th Edition, pages 980–982 (1996).
19. Factrel (gonadorelin HCl for subcutaneous or IV injection), Physician's Desk Reference, 50th Edition, pages 2877–2878 (1996).
20. Lupron (leuprolide acetate for subcutaneous injection), Physician's Desk Reference, 50th Edition, pages 2555–2556 (1996).
21. Lupron depot (leuprolide acetate for depot suspension), Physician's Desk Reference, 50th Edition, pages 2556–2562 (1996).
22. "Pharmaceutical Manipulation of Leuprorelin Acetate to Improve Clinical Performance", H. Toguchi, *J. of Intl. Medical Research*, 18, pages 35–41 (1990).
23. "Long-Term Stability of Aqueous Solutions of Luteinizing Hormone-Releasing Hormone Assessed by an In-Vitro Bioassay and Liquid Chromatography", Y. F. Shi, R. J. Sherins, D. Brightwell, J. F. Gallelli, D. C. Chatterji, *J. of Pharmaceutical Sciences*, 73/6, pages 819–821 (1984).
24. "Peptide Liquid Crystals: Inverse Correlation of Kinetic Formation and Thermodynamic Stability in Aqueous Solution", M. F. Powell, J. Fleitman, L. M. Sanders, V. C. Si, *Pharmaceutical Research*, 11/9, pages 1352–1354 (1994).
25. "Solution Behavior of Leuprolide Acetate, an LHRH Agonist, as Determined by Circular Dichroism Spectroscopy", M. E. Powers, A. Adejei, M. Y. Fu Lu, M. C. Manning, *Intl. J. of Pharmaceutics*, 108, pages 49–55 (1994).
26. "Preparation of Three-Month Depot Injectable Microspheres of Leuprorelin Acetate Using Biodegradable Polymers", *Pharmaceutical Research*, 11/8, pages 1143–1147 (1994).

The disclosure of each of the above publications, patents or patent applications is hereby incorporated by reference in its entirety to the same extent as if the language of each individual publication, patent and patent application were specifically and individually incorporated by reference.

Luteinizing hormone-releasing hormone (LHRH), also known as gonadotropin releasing hormone (GnRH), is a decapeptide with the structure:

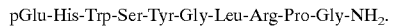

pGlu-His-Trp-Ser-Tyr-Gly-Leu-Arg-Pro-Gly-NH$_2$.

It is secreted by the hypothalamus and binds to receptors on the pituitary gland, releasing luteinizing hormone (LH) and follicle stimulating hormone (FSH). LH and FSH stimulate the gonads to synthesize steroid hormones. Numerous analogs of LHRH are known, including peptides related to LHRH which act as agonists and those which act as antagonists. [1–15] LHRH analogs are known to be useful for treating hormone-dependent diseases such as prostate cancer, benign prostatomegaly, endometriosis, hysteromyoma, metrofibroma, precocious puberty, or mammary cancer and as contraceptives. [8] Sustained release administration is preferred for both agonist LHRH-related compounds, which reduce the number of available receptors after repeated administration so that the production of steroid hormones is suppressed, and antagonist LHRH-related compounds, which must be continually administered for persistent inhibition of endogenous LHRH. [8]

The sustained parenteral delivery of drugs, especially peptide drugs, provides many advantages. The use of implantable devices for sustained delivery of a wide variety of drugs or other beneficial agents is well known in the art. Typical devices are described, for example, in U.S. Pat. Nos. 5,034,229; 5,057,318; and 5,110,596. The disclosure of each of these patents is incorporated herein by reference.

In general, oral bioavailability of peptides, including LHRH-related compounds, is low. [16–17]

Currently marketed formulations of LHRH, its analogs and related compounds which are used for parenteral injection are aqueous solutions which contain relatively low concentrations of LHRH-related compounds (0.05 to 5 mg/ml) and may also contain excipients such as mannitol or lactose. [18–20] Such formulations of LHRH-related compounds must either be stored refrigerated or may be stored at room temperature for short periods of time.

Available depot formulations of LHRH-related compounds administered for sustained release over a period of 1–3 months include a formulation comprised of 15% LHRH-related compound dispersed in a matrix of D,L-lactic and glycolic acids copolymer presented as a cylinder to be injected subcutaneously [1] and a formulation comprised of microparticles comprising a core of LHRH-related compound and gelatin surrounded by a shell of D,L-lactic and glycolic acids copolymer. These microparticles are suspended in a diluent for injection either subcutaneously or intramuscularly. [21, 26] These products must be stored at room temperature or lower. Aqueous formulations of LHRH-related compounds are known to exhibit both chemical and physical instability, as well as degradation after irradiation. [12–16, 22–25]

Formulations which have been shown to be stable ($t_{90}$ about five years) have been very low concentration (25 µg/ml) aqueous, buffered (10 mM, ionic strength of 0.15) solutions stored at temperatures no higher than room temperature (25° C.). [15]

There is a need for stable formulations of peptides.

SUMMARY OF THE INVENTION

The present invention provides stable non-aqueous formulations which are solutions of peptide compounds in non-aqueous protic solvents. In particular, formulations with concentrations of at least about 10% peptide are provided. These stable formulations may be stored at elevated temperatures (e.g., 37° C.) for long periods of time and are especially useful in implantable delivery devices for long term delivery (e.g., 1–12 month or longer) of drug.

In one aspect, the invention provides stable non-aqueous formulations of peptide compounds, said formulations comprising at least one peptide compound in at least one non-aqueous protic solvent. Particularly preferred formulations include at least about 10% (w/w) peptide compound.

In another aspect, the invention provides methods for preparing a stable non-aqueous formulation of an peptide compound, said methods comprising dissolving at least one peptide compound in at least one non-aqueous protic solvent. Preferred formulations comprise at least about 10% (w/w) peptide compound.

In yet a further aspect, the invention provides methods for treating a subject suffering from a condition which may be alleviated by administration of an peptide compound, said methods comprising administering to said subject an effective amount of a stable non-aqueous formulation comprising at least one peptide compound in at least one non-aqueous protic solvent.

DETAILED DESCRIPTION OF THE INVENTION

Figure 1:
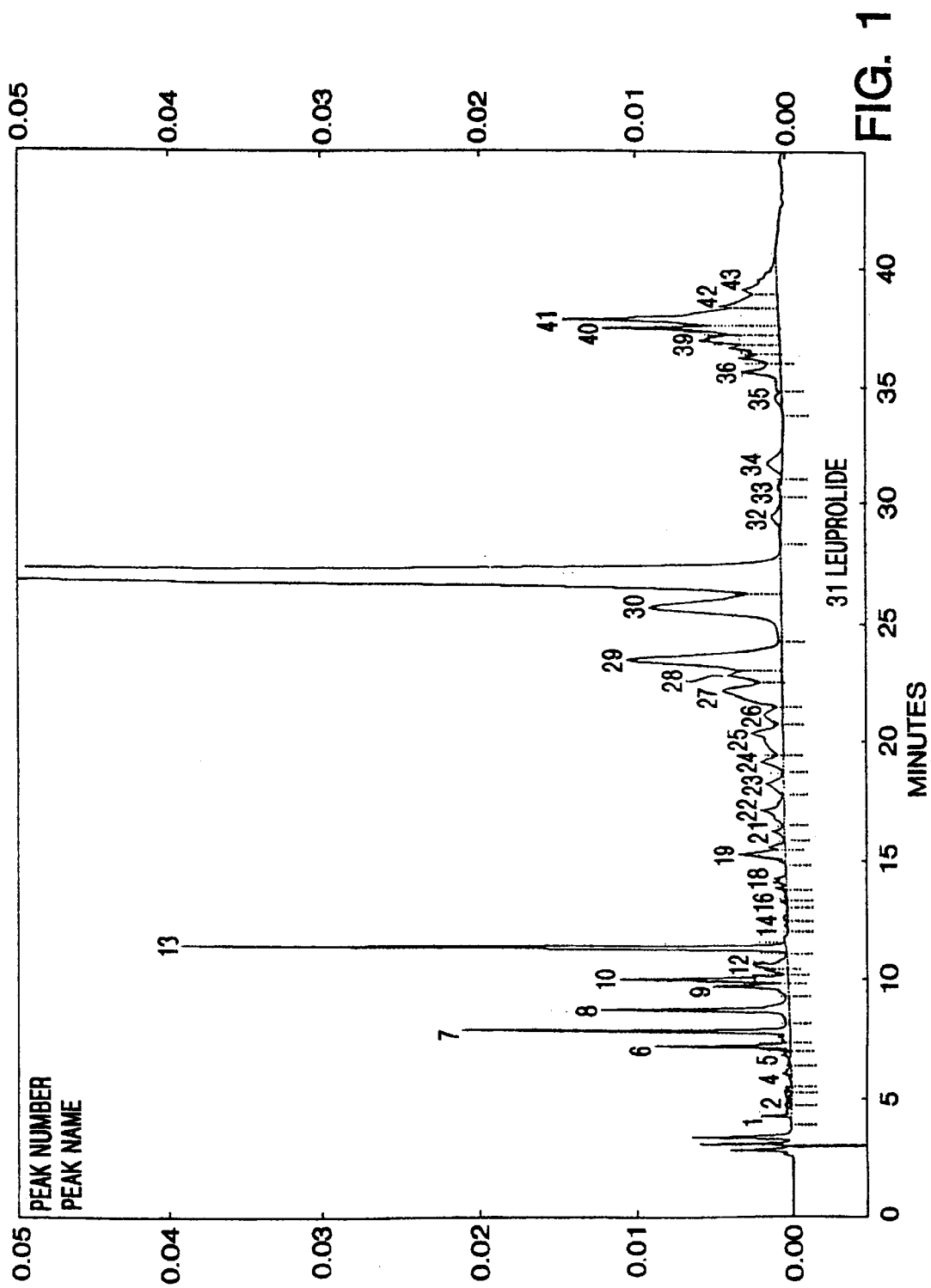
FIG. 1 illustrates the stability of 40% leuprolide acetate solution in propylene glycol (PG) after two months at 80° C. as measured by reverse phase HPLC (RP-HPLC).
Figure 2:
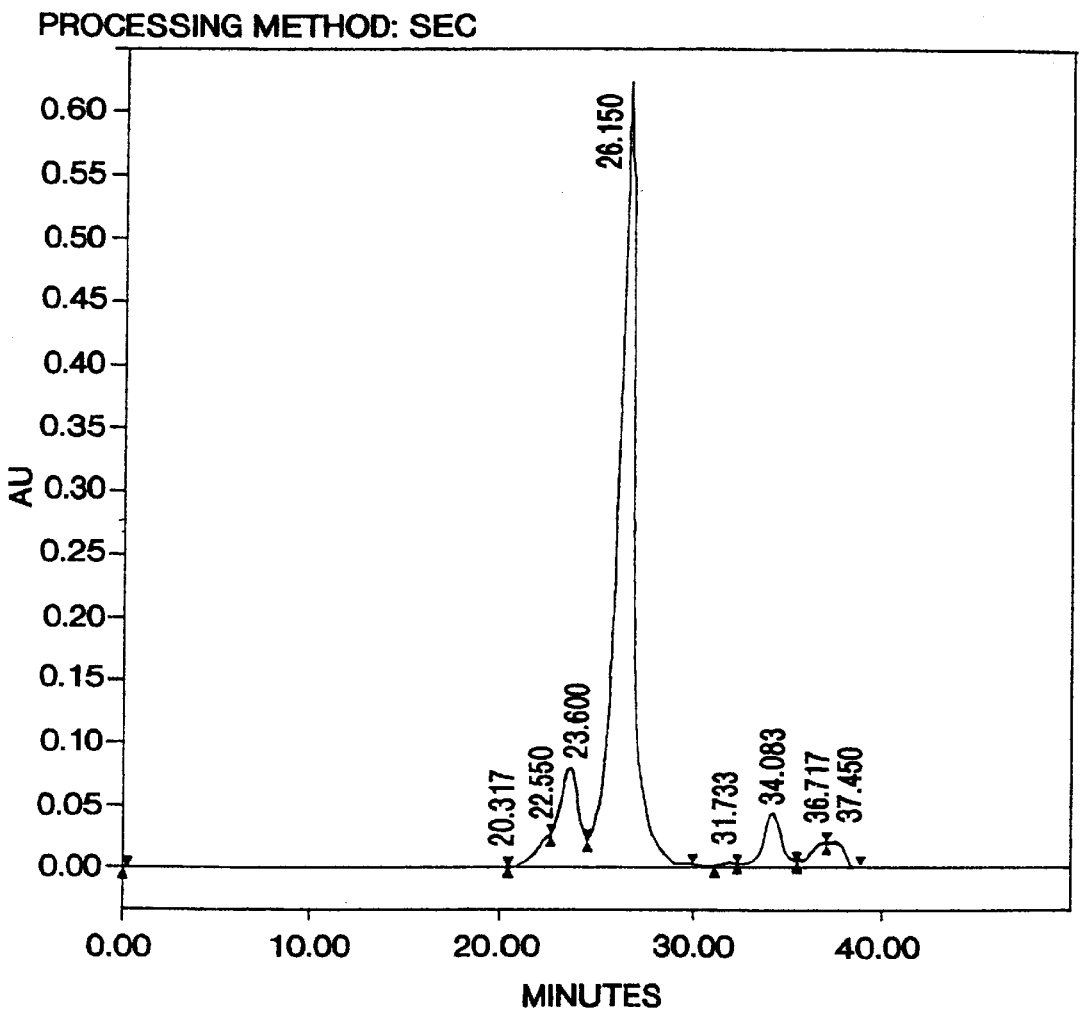
FIG. 2 shows RP-HPLC of the same sample as FIG. 1 injected on size exclusion chromatography (SEC) depicting 3% dimer and trimer formation with no higher order aggregates detected.

The present invention is drawn to the unexpected discovery that dissolving peptide compounds in non-aqueous protic solvents results in stable formulations. Previously known formulations of peptide compounds, which are dilute buffered aqueous solutions containing excipients such as EDTA or ascorbic acid which must be stored at low temperatures (4–25° C.), form degradation products using degradation pathways such as acid/base catalyzed hydrolysis, deamidation, racemization and oxidation. In contrast, the presently claimed formulations stabilize peptide compounds at elevated temperatures (e.g., 37° C. to 80° C.) and at high concentrations (i.e., at least about 10%).

Standard peptide and protein formulations consist of dilute aqueous solutions. Two critical aspects of peptide formulation include solubilization and stabilization of the drug molecule.

Peptide solubilization under aqueous conditions is standard, because it mimics nature. However, solubilization under non-aqueous conditions is not known. We have found that peptide formulation is possible in non-aqueous protic solvents.

Peptide stability is usually achieved by varying one or more of the following: pH, buffer type, ionic strength, excipients (EDTA, ascorbic acid, etc.). For these formulations, degradation pathways requiring water (hydrolysis, deamidation, racemization) cannot be fully stabilized. In contrast, in the present invention, highly concentrated peptides formulated in non-aqueous solutions such as propylene glycol and polyethylene glycol were shown to be chemically and physically stable. Such solvents are considered non-aqueous protic solvents. Some non-aqueous protic solvents may function to decrease the rate of degradation because they do not have large dipole moments needed for the stabilization of rate determining steps.

The invention consists of using non-aqueous protic solvents such as propylene glycol and polyethylene glycols to stabilize highly concentrated peptide and protein formulations against both chemical and physical degradation. The discovery consists of the realization that use of propylene glycol or polyethylene glycols improves the overall solubility and stability of peptides in a wide range of formulation conditions, including high concentrations and elevated temperatures, thus making possible the delivery of peptides in implantable delivery devices that would not otherwise be feasible.

A. Definitions

As used herein, the following terms have the following meanings:

The term "chemical stability" means that an acceptable percentage of degradation products produced by chemical pathways such as oxidation or hydrolysis is formed. In particular, a formulation is considered chemically stable if no more than about 20% breakdown products are formed after two months at 37° C.

The term "physical stability" means that an acceptable percentage of aggregates (e.g., dimers, trimers and larger forms) is formed. In particular, a formulation is considered physically stable if no more that about 15% aggregates are formed after two months at 37° C.

The term "stable formulation" means that at least about 65% chemically and physically stable peptide compound remains after two months at 37° C. (or equivalent conditions at an elevated temperature). Particularly preferred formulations are those which retain at least about 80% chemically and physically stable compound under these conditions. Especially preferred stable formulations are those which do not exhibit degradation after sterilizing irradiation (e.g., gamma, beta or electron beam).

The terms "peptide" and/or "peptide compound" mean polymers of up to about 50 amino acid residues bound together by amide (CONH) linkages. Analogs, derivatives, agonists, antagonists and pharmaceutically acceptable salts of any of these are included in these terms. The terms also include peptides and/or peptide compounds which have D-amino acids, modified, derivatized or non-naturally occurring amino acids in the D- or L-configuration and/or peptomimetic units as part of their structure.

The term "LHRH-related compound" means luteinizing hormone releasing hormone (LHRH) and its analogs and pharmaceutically acceptable salts. Octa-, nona- and decapeptide LHRH agonists and antagonists are included in the term LHRH-related compounds, as is native LHRH. Particularly preferred LHRH-related compounds include LHRH, leuprolide, goserelin, nafarelin, and other known active agonists and antagonists. [1–21]

The term "high concentration" means at least about 10% (w/w) and up to the maximum solubility of the particular compound.

The term "excipient" means a more or less inert substance in a formulation which is added as a diluent or vehicle or to give form or consistency. Excipients are distinguished from solvents such as EtOH, which are used to dissolve drugs in formulations, from non-ionic surfactants such as Tween 20, which are used to solubilize drugs in formulations, and from preservatives such as benzyl alcohols and methyl or propyl parabens, which are used to prevent or inhibit microbial growth.

The term "non-aqueous protic solvent" means a non-aqueous solvent which contains hydrogen attached to oxygen or nitrogen so that it is able to form hydrogen bonds or donate a proton. Examples of non-aqueous protic solvents are polyethylene glycols (PEGs), propylene glycol (PG), polyvinylpyrrolidone (PVP), methoxypropylene glycol (MPEG), glycerol and glycofurol.

The term "polar aprotic solvent" means a polar solvent which does not contain acidic hydrogen and does not act as a hydrogen bond donor. Examples of polar aprotic solvents are dimethylsulfoxide (DMSO), dimethylformamide (DMF), hexamethylphosphorotriamide (HMPT), and n-methyl pyrrolidone.

B. Preparation of Formulations

The present invention is drawn to non-aqueous formulations of peptide compounds in non-aqueous protic solvent which are stable for prolonged periods of time at elevated temperatures. Standard dilute aqueous peptide and protein formulations require manipulation of buffer type, ionic strength, pH and excipients (e.g., EDTA and ascorbic acid) to achieve stability. In contrast, the claimed formulations achieve stabilization of peptide compounds by the use of non-aqueous protic solvents. In particular, stability of high concentrations (at least about 10% w/w) of compound has been provided by the formulation of the present invention.

Examples of peptides and peptide compounds which may be formulated using the present invention include those peptides which have biological activity or which may be used to treat a disease or other pathological condition. They include, but are not limited to adrenocorticotropic hormone, angiotensin I and II, atrial natriuretic peptide, bombesin, bradykinin, calcitonin, cerebellin, dynorphin A, alpha and beta endorphin, endothelin, enkephalin, epidermal growth factor, fertirelin, follicular gonadotropin releasing peptide, galanin, glucagon, gonadorelin, gonadotropin, goserelin, growth hormone releasing peptide, histrelin, insulin, leuprolide, LHRH, motilin, nafarelin, neurotensin, oxytocin, somatostatin, substance P, tumor necrosis factor, triptorelin, and vasopressin. Analogs, derivatives, antagonists, agonists and pharmaceutically acceptable salts of the above may also be used.

The peptide compounds useful in the formulations and methods of the present invention can be used in the form of a salt, preferably a pharmaceutically acceptable salt. Useful salts are known to those of skill in the art and include salts with inorganic acids, organic acids, inorganic bases or organic bases. Preferred salts are acetate salts.

Peptides and peptide compounds which are readily soluble in non-aqueous protic solvents are preferred for use in the present invention. One of skill in the art can easily determine which compounds will be useful on the basis of their solubility, i.e., the compound must be soluble in the particular non-aqueous protic solvent to at least an acceptable amount, which may be a pharmaceutically effective amount. Preferred solubilities are at least about 10% (w/w). Particularly preferred peptide compounds are LHRH-related compounds, including leuprolide and leuprolide acetate.

The proportion of peptide may vary depending on the compound, the condition to be treated, the solubility of the compound, the expected dose and the duration of administration. (See, for example, *The Pharmacological Basis of Therapeutics,* Gilman et al., 7th ed. (1985) and *Pharmaceutical Sciences,* Remington, 18th ed. (1990), the disclosures of which are incorporated herein by reference.) The concentration of peptide in high concentration formulations may range from at least about 10% (w/w) to the maximum solubility of the compound. A referred range is from about 20 to about 60% (w/w). The currently more preferred range is from about 30 to about 50% (w/w) and a most preferred range is about 35 to about 45% (w/w).

Generally, the stable formulations of the present invention may be prepared by simply dissolving the desired amount of the desired peptide compound in the selected non-aqueous protic solvent. We have found that, for polymeric solvents such as PEG, solubility tends to be inversely proportional to the molecular weight of the solvent. Preferred non-aqueous protic solvents include propylene glycol (PG), polyethylene glycol (PEG), methoxypropylene glycol (MPEG), glycerol and polyvinylpyrrolidone (PVP).

It is known to those of skill in the art that water, buffer, solubilizers such as non-ionic surfactants, excipients such as EDTA and preservatives such as benzyl alcohols, methyl or propyl parabens may beneficially be added to pharmaceutical peptide formulations. (See, for example, *Pharmaceutical Sciences*, Remington, 18th ed. (1990).) Such agents may optionally be added to the claimed formulations.

C. Methodology

We have found that stable non-aqueous formulations of peptide compounds may be prepared by dissolving the peptide compound to be formulated in non-aqueous protic solvents.

We have tested these peptide compound formulations, specifically formulations of the LHRH-related compound leuprolide, for stability by subjecting them to accelerated aging at elevated temperature and measuring the chemical and physical stability of the formulations. Results of these studies (shown, for example, in Table III and FIGS. 1, 2, 6 and 7) demonstrate that these formulations were stable at conditions that approximate or exceed storage for one year at 37° C.

We have also tested peptide compound formulations prepared as described herein for stability after 2.5 megarad gamma irradiation. Results, shown in Table IV, show that these formulations remained chemically and physically stable after such irradiation. Formulations subjected to electron beam irradiation were also found to be stable.

As shown in Table I, we have tested a wide variety of peptide formulations, specifically leuprolide, goserelin, LHRH, bradykinin, insulin and trypsinogen, for stability by dissolving (or attempting to dissolve) them in water, then subjecting them to accelerated aging at elevated temperatures. The stability of the formulations was measured. Results are presented in Table I as half-life at 37° C. assuming an $E_a$=22.2 kcal/mole. A wide range of the peptides tested were soluble in the non-aqueous protic solvents tested and remained stable under the test conditions. The solubility of a particular peptide in water and the stability of the resulting solution are easily determined using routine procedures known to those of ordinary skill in the art.

TABLE I

Stability of Peptides in Non-Aqueous Protic Solvents

| FORMULATION | HALF-LIFE* (Temperature) |
|---|---|
| 40% Leuprolide in PG | 5.2 years (37° C.) |
| 40% Goserelin in PG | 6.2 years (80° C.) |
| 20% LHRH in PG | 1.2 years (65° C.) |
| 20% Bradykinin in PG | 3.2 months (65° C.) |
| 20% Insulin in PG | degraded w/in 24 hours (65° C.) |
| 40% Trypsinogen in PG | insoluble |
| 40% Trypsinogen in PEG | insoluble |
| 20% Trypsinogen in PEG | 7.7 months (65° C.) |

*Half-life at 37° C. assuming $E_a$ = 22.2 kcal/mole.

Formulations of 40% leuprolide in propylene glycol stored for six months at 37° C. showed linear degradation as measured by overall loss of peptide from the solution. Analysis of these data gave an activation energy ($E_a$) of 16.6 kcal/mole and a $t_{90}$ of 9.6 months, showing stability of these formulations at elevated temperatures.

We have also unexpectedly found that certain peptide formulations of the present invention are bacteriostatic (i.e., inhibit bacterial growth), bactericidal (i.e., cause the death of bacteria), and sporicidal (i.e., kill spores). In particular, leuprolide formulations of 50–400 mg/ml exhibited bacteriostatic, bactericidal and sporicidal activity. The stability of the samples was unaffected by spiking with bacteria, indicating that the enzymes released from the killed and lysed bacteria did not adversely affect the stability of the product. This demonstrates that these formulations were not conducive to enzymatic activity.

Some peptides, for example calcitonin and leuprolide, are known to be physically unstable, exhibiting aggregation, gelation and fibrillation when formulated in solution in non-aqueous protic solvents as well as in aqueous solution. For example, leuprolide can be induced to gel by increasing peptide concentration, introduction of salts or gentle agitation. Improving physical stability can allow for easier parenteral administration, including administration using implantable drug delivery systems.

It has unexpectedly been found that adding polar aprotic solvents such as DMSO to non-aqueous protic solvent formulations of certain peptides, such as leuprolide, goserelin and calcitonin, prevents gelation of the formulation. This is apparently because non-aqueous polar aprotic solvents cause peptides to form a random coil/alpha helix conformation that does not refold into a beta sheet structure and, therefore, does not gel. Thus, these solvents have an anti-gellant effect.

Additionally, the stability of liquid and gelled (by agitation) leuprolide formulations in the non-aqueous protic solvent PG (370 mg/ml) was studied in vitro at 37° C. and in vivo in rats, respectively. Results are presented in Table II, and show that the both gelled and liquid formulations remained stable over a period of 12 weeks.

TABLE II

Stability Studies of Liquid and Gelled Leuprolide Formulations in PG

| STUDY | TIME (weeks) | LIQUID (% remaining) | GELLED (% remaining) |
|---|---|---|---|
| Long Term Stab | 6 | 98.50 | |
| Long Term Stab | 12 | 98.00 | |
| Rat | 6 | | 97.40 |
| Rat | 12 | | 95.90 |

A major aspect of the invention is that non-aqueous solutions containing peptide compounds in non-aqueous protic solvents are stable at high temperatures for long periods of time. Such formulations are stable even when high concentrations are used. Thus, these formulations are advantageous in that they may be stored for long time periods at or above room temperature. They are also suitable for use in implantable delivery devices.

DISCLOSURE OF EXAMPLES OF THE INVENTION

The following methods were used to perform the studies in the Examples that follow.

1. Preparing Leuprolide Acetate Solutions

Leuprolide acetate (obtained, for example, from Mallinckrodt, St. Louis, Mo.) was weighed and dissolved using heat (80° C.), swirling, agitation and/or centrifugation as needed, in vehicle (PG, PEG, MPEG, PG/H$_2$O, PG/H$_2$O, PEG/PG, MPEG/H$_2$O, or PG with EDTA) at the appropriate concentration (w/w). Unless otherwise noted the term PEG means PEG 300. The term dry PG refers to PG formulations prepared in a low moisture environment (i.e., dry N$_2$ atmosphere).

Unless otherwise noted, leuprolide free base content was calculated from certificate of analysis potency values to be 37% free base. This was 40% leuprolide acetate, except as noted.

2. Preparation of Reservoirs

The reservoirs of implantable drug delivery devices (as disclosed in U.S. patent application Ser. No. 08/595,761, incorporated herein by reference) were filled with the appropriate leuprolide acetate solution. The filled devices then underwent stability testing. The formulation was filled into titanium or polymer reservoirs with a polymeric plug blocking each end. The filled reservoir was then sealed in a polyfoil bag and placed in a stability testing oven.

It should be noted that the formulations inside the reservoirs of these devices are completely isolated from the outside environment.

3. Reverse Phase-HPLC (RP-HPLC)

All stability samples were analyzed for leuprolide concentration and % peak area using a gradient elution reversed-phase HPLC assay with a refrigerated autosampler (4° C.) to minimize sample degradation. The chromatographic conditions used are listed below.

RP-HPLC Chromatographic Conditions

| Description | Parameter |
|---|---|
| Column | HaiSil C18, 4.6 × 250 mm, S/N 5103051 |
| Flow Rate | 0.8 mL min$^{-1}$ |
| Injection Volume | 20 µL |
| Detection | 210 nm |
| Leuprolide Retention Time | Between 25–30 minutes |
| Mobile Phase | A = 100 mM Sodium Phosphate, pH 3.0<br>B = 90% Acetonitrile/Water |
| Gradient | Minutes  0   5    25    40  41  46  46.1  50<br>% B       15  26.5 26.5  65  85  85  15    15 |

Leuprolide standards (in water) at 4 to 6 different concentration levels, typically between 0.1–1.2 mg/mL, were run along with the stability samples. The stability samples were bracketed by the standard sets, with no more than 40 samples in between the standard sets. All peaks between the void volume and 45 minutes of the run were integrated. The integrated peak areas for the leuprolide standards were plotted as a function of the concentration. The leuprolide concentrations for the stability samples were then calculated using linear regression. The % peak areas for the leuprolide peak, the sum of all the peaks eluting before leuprolide (labeled "others"), and the sum of all the peaks eluting after leuprolide (labeled "aggregates") were also recorded and plotted as a function of the sample time points.

4. Size Exclusion Chromatography (SEC)

Selected stability samples were analyzed for % peak area and molecular weights using an isocratic solution SEC assay with a refrigerated autosampler (4° C.). The chromatographic conditions used are listed below.

SEC Chromatographic Conditions

| Description | Parameter |
|---|---|
| Column | Pharmacia Peptide, HR 10/30, 10 × 300 mm |
| Flow Rate | 0.5 mL min$^{-1}$ |
| Injection Volume | 20 µL |
| Detection | 210 nm |
| Leuprolide Retention Time | Approximately 25 minutes |
| Mobile Phase | 100 mM Ammonium Phosphate, pH 2.0,<br>200 mM Sodium Chloride, 30% Acetonitrile |

The void volume and total volume for the size exclusion column was needed for the calculation of the molecular weights. The Bio-Rad high molecular weight standard and 0.1% acetone were used to determine the void volume and total volume respectively. The retention times for the first peak in the Bio-Rad standard and the acetone peak were recorded and converted to volume units using the equations below. Since these values are constant for a particular SEC column and HPLC system, the void and total volumes were redetermined whenever changes to the SEC column or HPLC system were made. A standard run was then made followed by the stability samples. The standard mixture contained approximately 0.2 mg/mL of the following peptides: Bursin (MW=449), WLFR peptide (MW=619), Angiotensin (MW=1181), GRF (MW=5108), and Cytochrome C (MW=12394). These standards were chosen because they bracketed leuprolide molecular weight and all had basic pI (9.8–11.0), similar to leuprolide.

The % peak areas were recorded for all the peaks. The molecular weights for the species separated were calculated using the equations below.

$V_s$=flow rate (mL/min)×sample peak retention time (min)

$V_o$=flow rate (mL/min)×void volume peak retention time (min)

$V_t$=flow rate (mL/min)×total volume peak retention time (min)

$$Kd = \frac{V_s - V_o}{V_t - V_o}$$

Where:
$V_s$=standard or sample volume
$V_o$=void volume
$V_t$=total volume $V_s$ was calculated to each peptide standard peak. Kd for each peptide standard was then calculated using the values for $V_t$ and $V_o$ determined earlier. The linear regression line from the plot of logMW vs. Kd$^{-1}$ was used to determine the molecular weights for each peak in the stability sample. The % peak areas for the stability samples were also recorded.

5. Instrumentation and Materials

The instrumentation and materials used for RP-HPLC and SEC were as follows:

Waters Millennium HPLC system consisting of 717 autosampler, 626 pump, 6000S controller, 900 photodiode array detector, and 414 refractive index detector (Waters Chromatography, Milford, Mass.)

HPLC vials, for 48-position and 96-position (Waters Chromatography, Milford, Mass.)

HaiSil C18, 120 A, 5 µm4.6×250 mm HPLC column (Higgins Analytical, Mountain View, Calif.)

Pharmacia Peptide, HR 10/30 SEC column (Pharmacia Biotech, Piscataway, N.J.)

6. Purity

Stability samples were analyzed using RP-HPLC. The area under the curve for the leuprolide peak divided by the sum of the areas under the curve of all peaks gave % purity. [It should be noted that the data for % concentration presented with the % purity data (Examples 6, 8, 9 and 10) are inconclusive. The analysis methods used to determine % concentration in these experiments were unreliable.]

The following examples are offered to illustrate this invention and are not meant to be construed in any way as limiting the scope of this invention.

EXAMPLE 1

Accelerated Stability Studies of Leuprolide Acetate Formulations

Formulations of 40% (w/w) leuprolide acetate (equivalent to 37% leuprolide free base) in vehicle were prepared as described above and used to fill the reservoirs of implantable drug delivery devices, also as described above. Some reservoirs were made of polymer materials, while some were titanium.

The filled devices were subjected to accelerated aging by storing them at elevated temperatures (80–88° C.) for seven days in an incubator (Precision Scientific or Thelco). This is equivalent to about six months at 37° C. or about one year at room temperature (25° C.), assuming an activation energy ($E_a$) of 16.6 kcal/mole.

The samples were analyzed using RP-HPLC and SEC as described above to determine the chemical and physical stability of the aged formulations.

Results, presented in Table III, demonstrate that these formulations were able to maintain the stability of the LHRH-related compound leuprolide. In each case, at least 65% leuprolide was retained.

TABLE III

Stability of Leuprolide Acetate Non-Aqueous Protic Formulations After 7 Days at Elevated Temperatures

| Temperature (° C.) | Reservoir Material | Formulation | % Leuprolide at Day 7 |
|---|---|---|---|
| 88 | Polymer | 40% in PG | 70 |
| 88 | Polymer | 40% in PG/H$_2$O (70/30) | 73 |
| 88 | Polymer | 40% in PEG/H$_2$O (90/10) | 77 |
| 88 | Titanium | 40% in PG | 87 |
| 88 | Polymer | 20% in PEG/PG(50/50) | 74 |
| 88 | Polymer | 20% in PEG/H$_2$O(88/12) | 68 |
| 80 | Polymer | 40% in PG | 74 |
| 80 | Titanium | 40% in PG | 80 |
| 80 | Titanium | 40% in PEG/H$_2$O(90/10) | 86 |
| 80 | Titanium | 40% in PG | 87 |
| 80 | Titanium | 40% in PG | 80 |
| 80 | Titanium | 40% in 1% EDTA in PG | 80 |
| 80 | Polymer | 40% in MPEG 350/H$_2$O(50/50) | 83 |
| 80 | Titanium | 40% in dry PG | 76 |

EXAMPLE 2

Stability Studies of Irradiated Leuprolide Acetate Formulations

Formulations of 40% (w/w) as received leuprolide acetate (equivalent to 37% leuprolide free base) in PG were prepared as described above and used to fill the reservoirs of drug delivery devices, also as described above. All reservoirs were made of polymer materials.

The filled devices were subjected to 2.5 megarad gamma irradiation. Samples were shipped to Sterigenics (Tustin, Calif.) and gamma irradiated (Cobalt 60) in batch mode. Samples labeled "cold" were shipped and irradiated on dry ice. Samples were then subjected to accelerated aging as in Example 1. Samples were taken at day 0 and day 7, and analyzed using RP-HPLC and SEC as described above to determine the chemical and physical stability of the irradiated formulations.

Results, presented in Table IV, demonstrate that these leuprolide acetate formulations were stable after irradiation. In every case, at least 65% leuprolide was retained, with low levels of aggregate formation.

TABLE IV

Stability of 40% (w/w) Leuprolide Acetate Protic Formulations After 2.5 Megarad Gamma Irradiation in Polymer Reservoirs

| Formulation | Irradiation | % Leuprolide at Day 7 (RP-HPLC) | SEC Day 0 | | SEC Day 7 | |
|---|---|---|---|---|---|---|
| | | | % monomer | % dimer/trimer | % monomer | % dimer/trimer |
| 40% in PG | Yes | 88 | 97.4 | 0.9 | 94.5 | 3.7 |
| 40% in PG | No | 75 | 98.8 | 0.03 | 91.9 | 5.9 |
| 40% in PG | Cold | 75 | 98.3 | 0.2 | 92.2 | 5.6 |

EXAMPLE 3

Solubility Studies of Leuprolide Acetate in PG

Leuprolide acetate formulations in PG were prepared as described above. Formulations were heated at 80° C. to accelerate the dissolution of leuprolide in PG. The data are presented in Table V below.

TABLE V

% Leuprolide in PG

| Wt. Leuprolide Acetate (mg) | Wt. PG (mg) | Total Wt. | % Leuprolide Acetate |
|---|---|---|---|
| 148.6 | 225.7 | 374.3 | 39.70 |
| 154 | 183.7 | 337.7 | 45.60 |
| 146.8 | 147.2 | 294 | 49.93 |

EXAMPLE 4

Long Term Accelerated Stability Studies of Leuprolide Acetate in PG

Solutions of 40% leuprolide acetate (w/w) in PG were prepared, loaded into reservoirs, stored for two months at 80° C. and analyzed as described above. Results, shown in FIGS. 1 (RP-HPLC) and 2 (SEC) show that 55.9% leuprolide was recovered, with only 37.2% chemical degradation and 15.2% physical aggregation after the two month period. These formulations were stable (as defined above) after seven days at 80° C., which corresponds to two months at 37° C.

Figure 5:
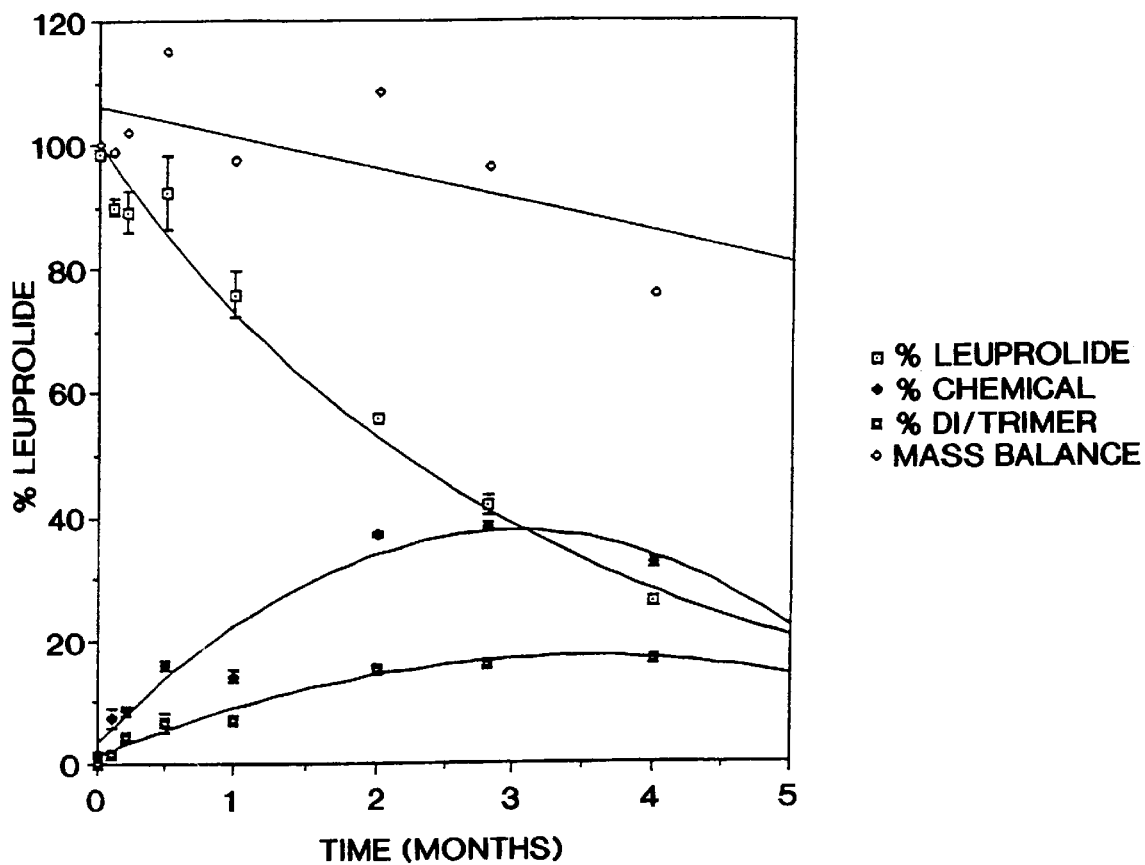
FIG. 5 illustrates the chemical and physical stability of a 40% leuprolide solution in PG after four months at 80° C.
Figure 6:
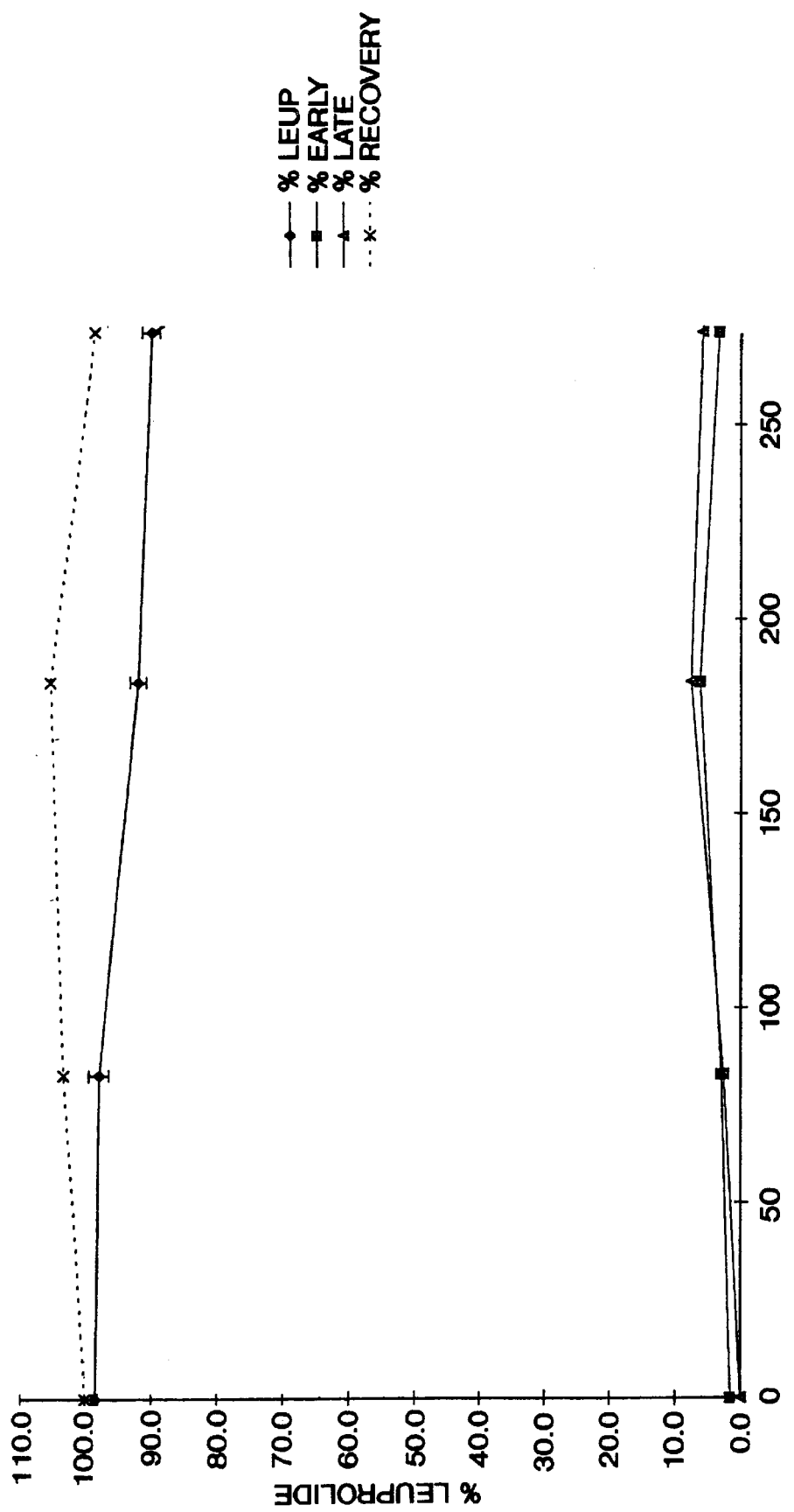
FIG. 6 illustrates the chemical stability of a 40% leuprolide acetate solution in PG after nine months at 37° C.
Figure 7:
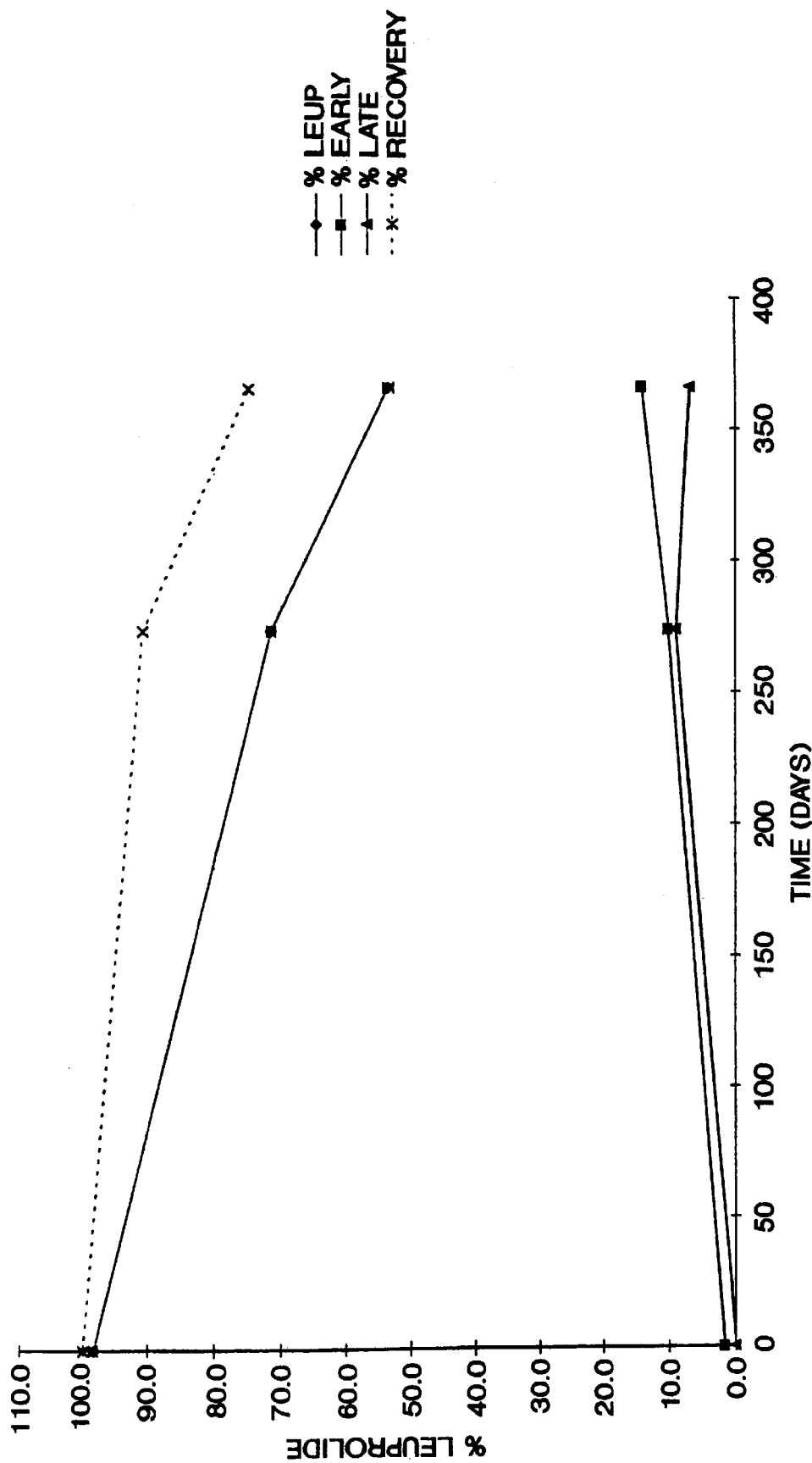
FIG. 7 illustrates the chemical stability of a 40% leuprolide acetate solution in PG/acetate buffer (30:70) after one year at 37° C.

Solutions of 40% leuprolide acetate (w/w) in PG were prepared, loaded into reservoirs, stored at 80° C. for four months and analyzed using RP-HPLC as described above. FIG. 5 is a plot of leuprolide, and its chemical and physical degradation products recovered over the four month time period. The sum of these three elements is also presented as mass balance. The results show that we can account for all the peptide material as either intact leuprolide or a degradation species, indicating that stability studies are not missing an unknown degradation process or product.

Figure 3:
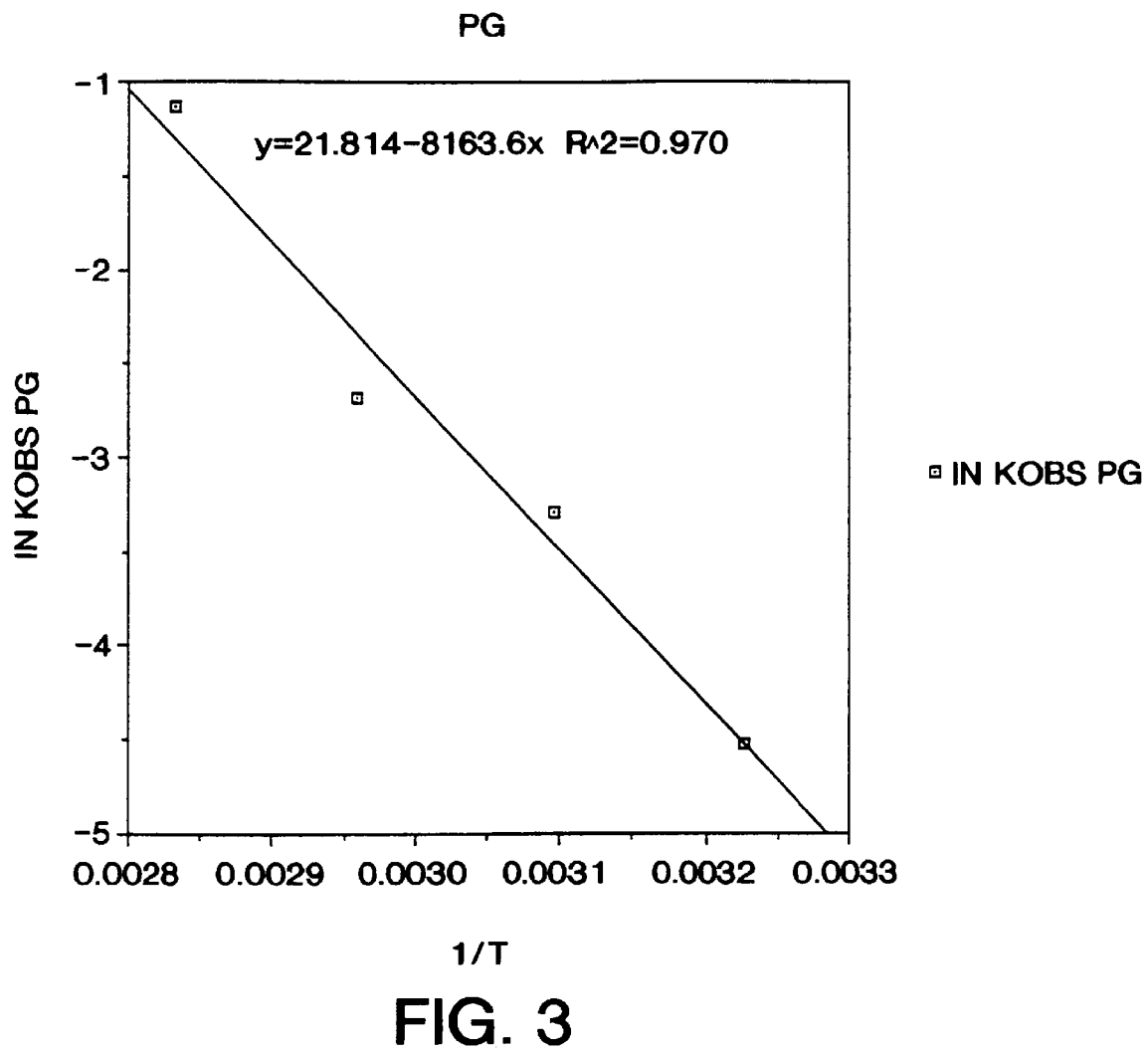
FIG. 3 presents the Arrhenius plot showing the loss of leuprolide from 40% solutions of leuprolide acetate in propylene glycol (PG).
Figure 4:
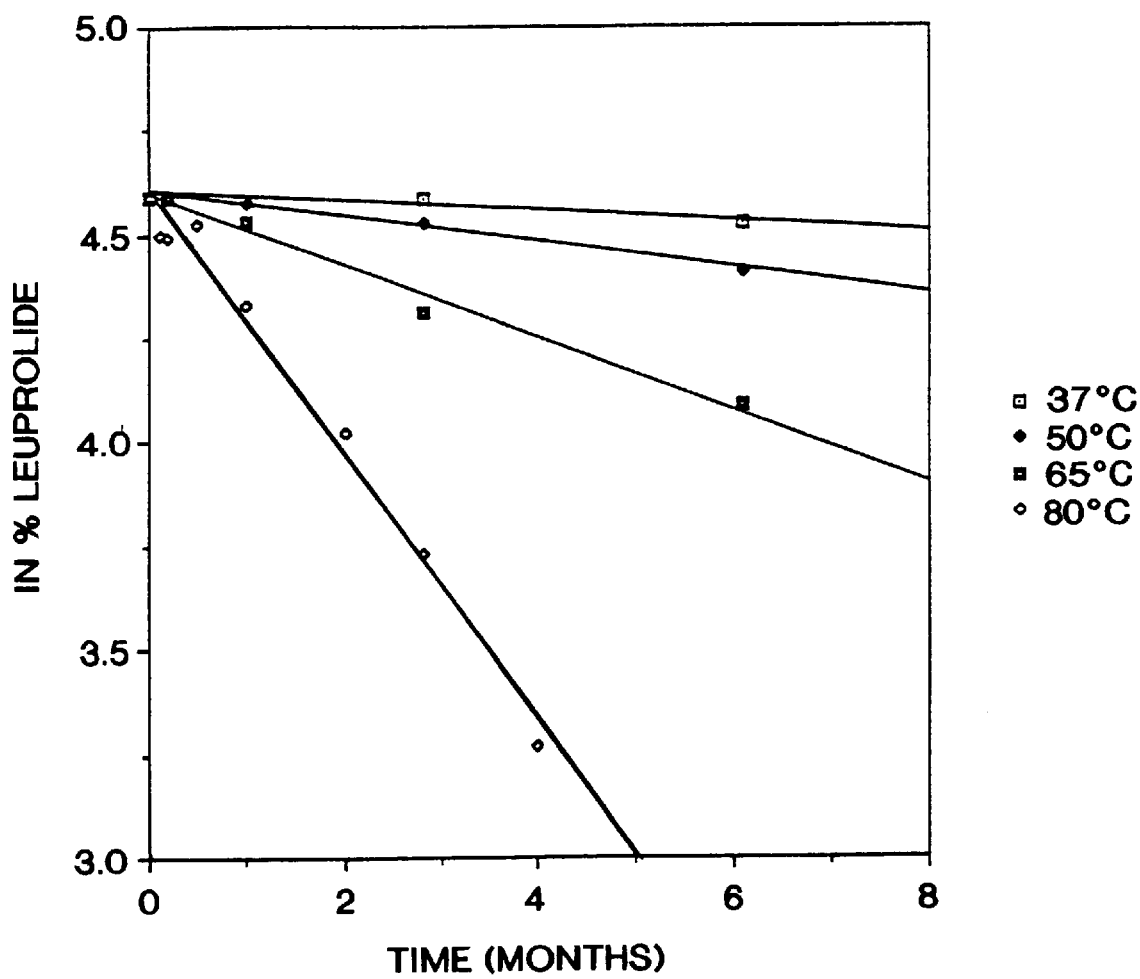
FIG. 4 illustrates the loss of leuprolide from a 40% leuprolide solution in PG over a period of four to six months at 37° C., 50° C., 65° C. or 80° C.

Solutions of 40% leuprolide acetate (w/w) in PG were prepared, loaded into reservoirs, stored at 37° C., 50° C., 65° C. or 80° C. for four to six months and analyzed using RP-HPLC as described above. Results, presented in FIG. 4, show that leuprolide degradation fits pseudo first order kinetics. Furthermore, as discussed below, FIG. 3 indicates that leuprolide in PG degradation fits linear Arrhenius kinetics. Therefore, accelerated stability studies are a valid technique for assessing the stability of leuprolide and extrapolating back to 37° C.

Solutions of 40% leuprolide acetate (w/w) in PG were prepared, loaded into reservoirs, stored at 37° C., 50° C., 65° C. or 80° C. and analyzed using RP-HPLC as described above. Results were calculated as described in *Physical Pharmacy: Physical Chemical Principles in the Pharmaceutical Sciences,* 3rd ed., Martin et al., Chapter 14 (1983) and showed the $E_a$ of these solutions to be 16.6 kcal/mole with a $t_{90}$ of 9.6 months at 37° C. The data are shown below and an Arrhenius plot of the data is presented in FIG. 3.

| | PG | |
|---|---|---|
| ° C. | Kobs (months$^{-1}$) | t½ (months) |
| 37 | 1.12 × 10$^{-2}$ | 61.6 |
| 50 | 3.13 × 10$^{-2}$ | 22.2 |
| 65 | 8.64 × 10$^{-2}$ | 8.0 |
| 80 | 0.322 | 2.4 |

$E_a$ = 16.6 kcal/mole

EXAMPLE 5

Long Term Stability Studies of Leuprolide Acetate in PG

The chemical stability of 40% leuprolide acetate solutions prepared and analyzed as described above is presented in FIG. 6. After nine months at 37° C. more than 90% (90.1%) leuprolide was present, with less than 5% (3.1%) chemical degradation products (shown as "early") and less that 10% (5.6%) physical aggregation (shown as "late"), based on RP-HPLC data but in good agreement with SEC data, being formed.

EXAMPLE 6

Long Term Stability Studies of Leuprolide Acetate in PG/Acetate Buffer

Figure 8:
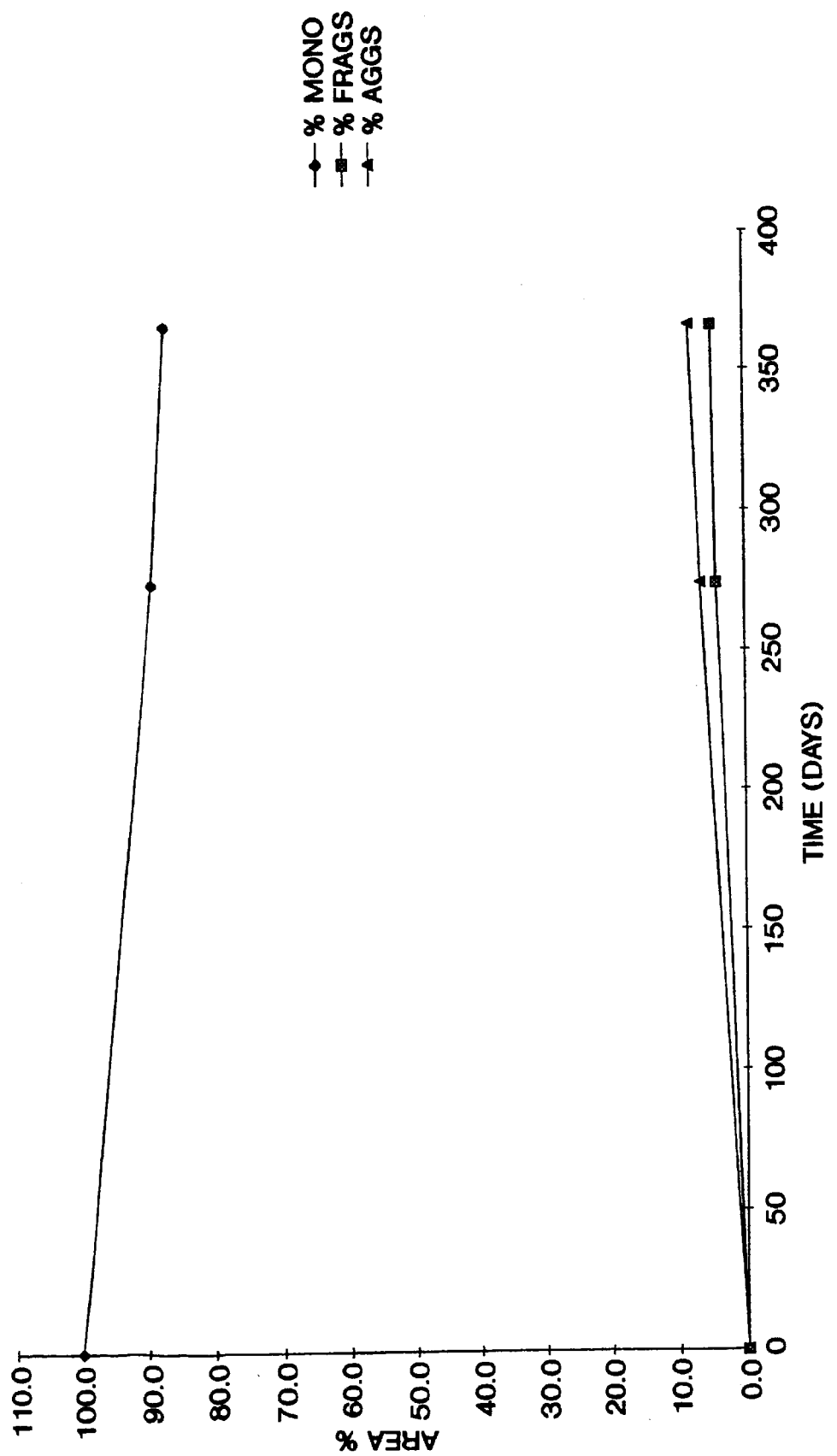
FIG. 8 illustrates the physical stability of a 40% leuprolide acetate solution in PG/acetate buffer (30:70) after one year at 37° C.

Solutions of 30% leuprolide acetates (w/w) in PG/acetate buffer (pH 5.0, 0.0282 M) (30:70) were prepared as described above then loaded into glass ampules, irradiated as described above and stored at 37° C. for one year. Analysis (as described above) by RP-HPLC (FIG. 7) and SEC (FIG. 8) showed that these formulations were stable. After nine months, RP-HPLC showed that over 70% chemically active leuprolide was present in the formulations. SEC results showed that 90% physically stable leuprolide was present after 9 months at 37° C.

EXAMPLE 7

Long Term Accelerated Stability Studies of Leuprolide Acetate in PG/Water

Formulations of 40% leuprolide acetate (w/w) in PG/water with preservatives (30:70) were prepared by mixing 0.18% methyl paraben and 0.025% propylparaben with water, preparing a 30:70 PG/water with preservative solution and dissolving the leuprolide acetate in this solution as described above. Formulations were loaded into glass ampules, then irradiated and stored at 60° C. as described above.

Figure 9:
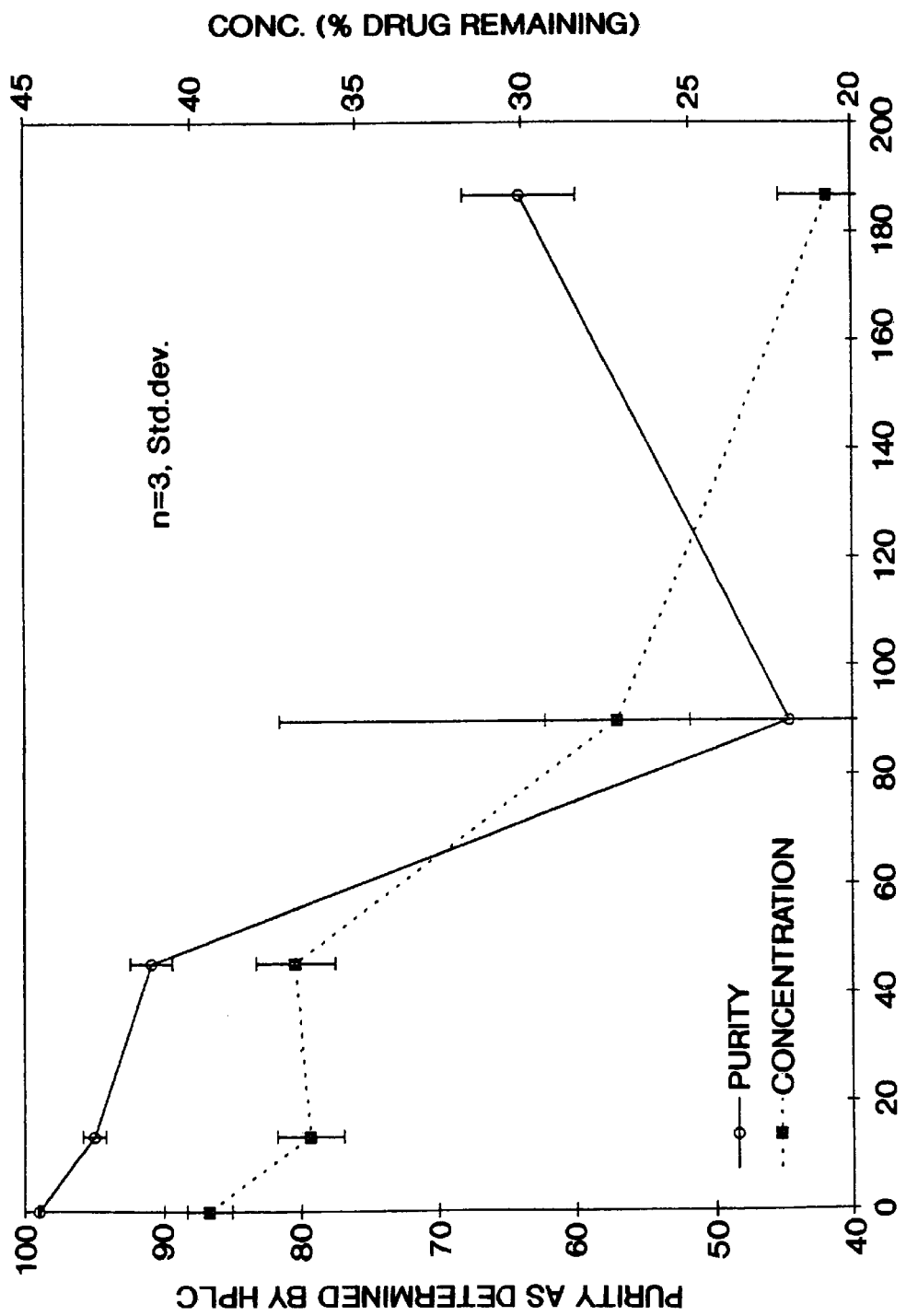
FIG. 9 illustrates the stability of a 40% leuprolide acetate solution in PG/water with preservatives (30:70) after six months at 60° C. after irradiation.

Purity was assayed over a six month period as described above. Results are presented in FIG. 9. These data show that these formulations had purity of over 90% at 45 days and about 65% at six months. The 90 day data point showed a very high standard deviation.

EXAMPLE 8

Long Term Stability Studies of Leuprolide Acetate in PG/Water

Formulations of 40% leuprolide acetate (w/w) in PG/water (30:70) were prepared as described above, loaded into glass ampules, irradiated and stored at 37° C. for six months as described above, then assayed using HPLC.

Figure 10:
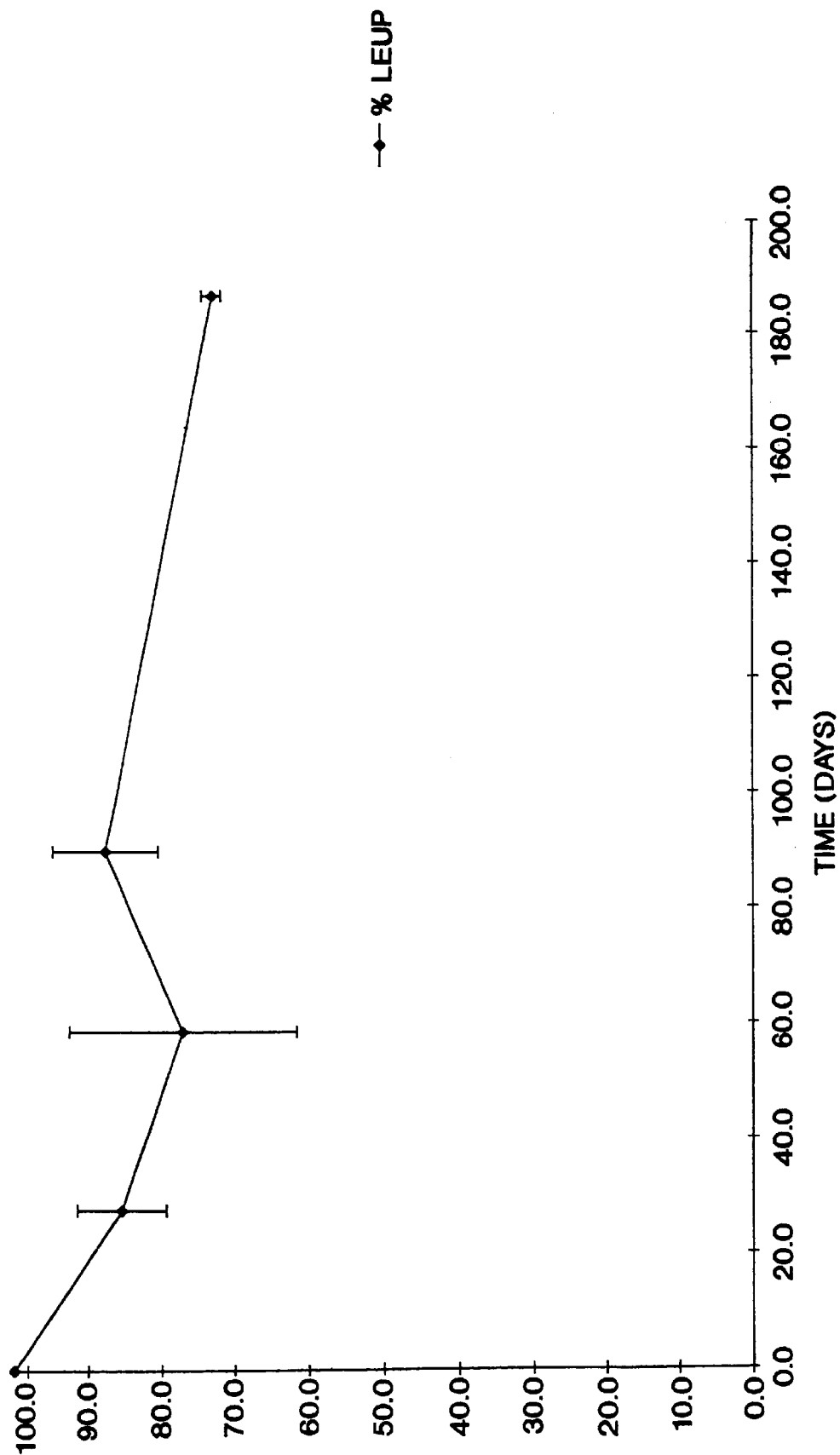
FIG. 10 illustrates the long term stability of a 40% leuprolide acetate solution in PG/water (30:70) over a six month period at 37° C. after irradiation.

Results, presented in FIG. 10, showed that over 70% leuprolide remained after six months.

EXAMPLE 9

Accelerated Stability Studies of Goserelin in PEG 600/Acetate Buffer

Formulations of 30% goserelin (w/w) in PEG 600/acetate buffer (30:70), prepared as described above for leuprolide acetate, were stored in glass ampules for 14 days at 80° C. and analyzed for purity as described above.

Figure 11:
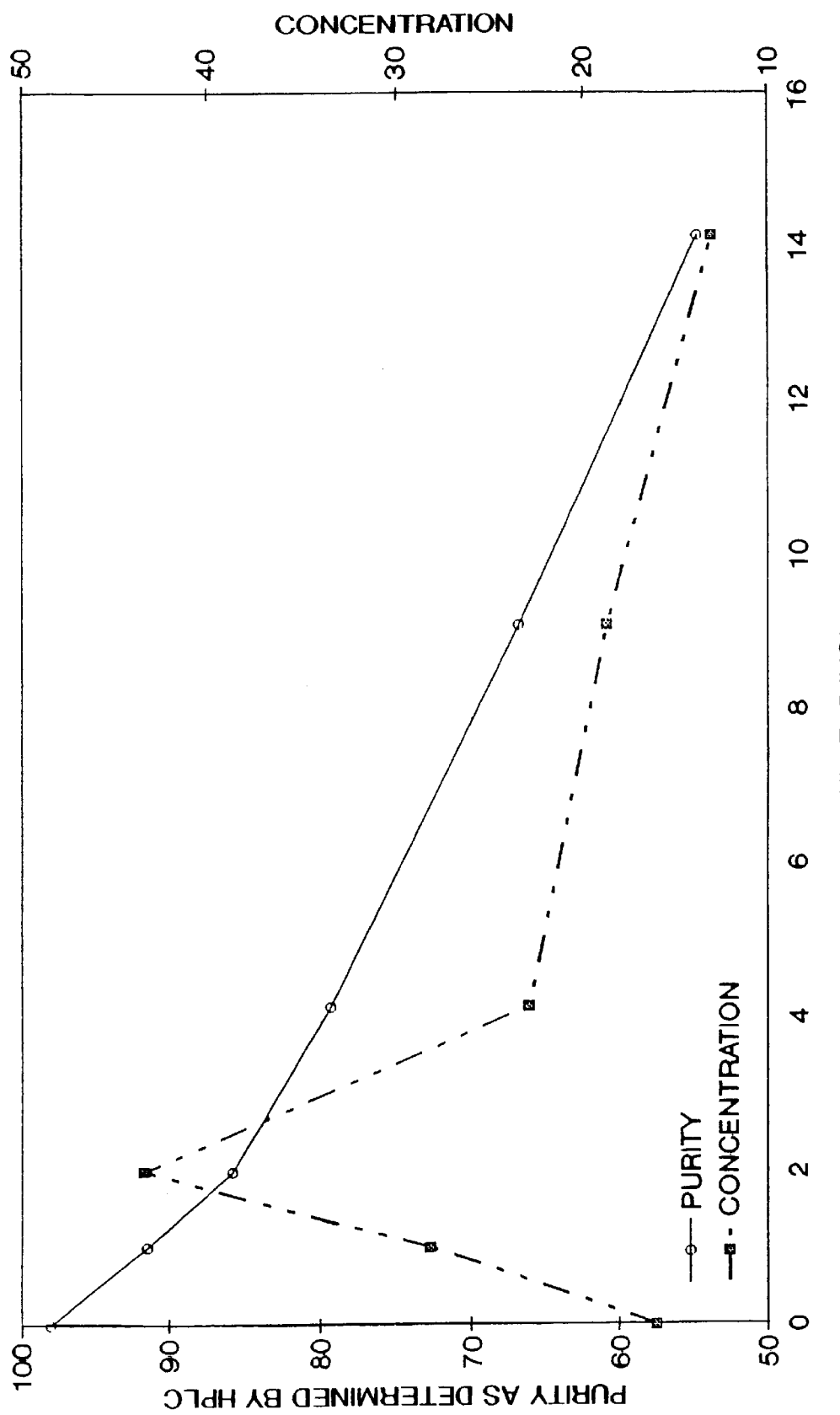
FIG. 11 illustrates the stability of a 30% goserelin solution in PEG 600/acetate buffer (30:70) after 14 days at 80° C.

Results in FIG. 11 show that after nine days over 65% goserelin remained.

EXAMPLE 10

Stability Studies of Goserelin Formulations

Formulations of 40–45% (w/w) goserelin in either PEG 600 or PG/acetate buffer (30:70) were prepared as described above and placed in polymeric containers. The containers were stored at 37° C. for one month in an incubator. The samples were analyzed using RP-HPLC to determine the chemical stability of the aged formulations.

Results, presented below, demonstrate that these formulations were able to maintain the stability of the LHRH-related compound goserelin. In each case, at least 98% goserelin was retained, as indicated by the purity data.

| DRUG | VEHICLE | % PURITY | % CONCENTRATION |
|---|---|---|---|
| goserelin | PEG 600 | 99.3 | 23.6 |
| goserelin | PG/Acetate Buffer (30:70) | 98.2 | 49.7 |

EXAMPLE 11

Stability Studies of Nafarelin Formulations

Formulations of 15% (w/w) nafarelin in either PEG 600 or propylene glycol were prepared as described above for leuprolide and placed in polymeric containers.

The containers were stored at 37° C. for one month in an incubator.

The samples were analyzed using RP-HPLC to determine the chemical stability of the aged formulations.

Results, presented below, demonstrated that these formulations were able to maintain the stability of the LHRH-related compound nafarelin. In each case, at least 99% nafarelin was retained, as indicated by the purity data.

| DRUG | VEHICLE | % PURITY | % CONCENTRATION |
|---|---|---|---|
| nafarelin | PEG 600 | 99.4 | 15.8 |
| nafarelin | PG | 99.4 | 12.9 |

Modification of the above-described modes of carrying out various embodiments of this invention will be apparent to those of skill in the art following the teachings of this invention as set forth herein. The examples described above are not limiting, but are merely exemplary of this invention, the scope of which is defined by the following claims.

What is claimed is:

1. A method for treating a subject suffering from a condition which may be alleviated by administration of a peptide compound comprising administering to said subject an effective amount of a stable non-aqueous formulation of a peptide compound comprising:

a) at least one peptide compound; and
   b) at least one non-aqueous protic solvent.

2. The method of claim 1 wherein said administration is parenteral administration.

3. The method of claim 1 wherein said administration is long-term continuous administration.

4. The method of claim 1 wherein said administration is accomplished by use of an implantable drug delivery device.

5. The method of claim 1 wherein said condition is prostatic cancer and said peptide compound is leuprolide.

6. The method of claim 1 wherein at least about 80 micrograms of leuprolide is administered daily.

7. The method of claim 6 wherein said daily administration continues for a period selected from the group consisting of 3 months, 6 months and 12 months.

8. The method of claim 7 wherein said daily administration for said period is continuous administration accomplished using an implantable drug delivery system.

9. The method of claim 1 wherein said condition is prostatic cancer and said peptide compound is an LHRH antagonist.

10. The method of claim 1 wherein said peptide compound is an LHRH-related compound.

11. The method of claim 1 wherein said peptide compound is selected from the group consisting of leuprolide, LHRH, nafarelin and goserelin.

12. The method of claim 1 wherein said at least one non-aqueous protic solvent is selected from the group consisting of PG, PEG and glycerol.

13. The method of claim 1 wherein said administration continues for 12 months.

* * * * *